United States Patent [19]

Hawthorne et al.

[11] 3,976,596

[45] Aug. 24, 1976

[54] HYDRIDOMETALLIC CARBORANE CATALYTIC COMPOUNDS

[75] Inventors: Marion F. Hawthorne, Brentwood, Calif.; Timm E. Paxson, Houston, Tex.

[73] Assignee: The United States of America as represented by the Secretary of the Navy, Washington, D.C.

[22] Filed: Mar. 26, 1975

[21] Appl. No.: 562,070

[52] U.S. Cl............................. 252/431 P; 260/429 R; 260/448.2 B; 260/497 R; 260/526 R; 260/561 R; 260/604 HF
[51] Int. Cl.²...................... B01J 31/12; C07F 15/00
[58] Field of Search .............. 260/429 R; 252/431 P

[56] References Cited
UNITED STATES PATENTS

| | | | |
|---|---|---|---|
| 3,418,346 | 12/1968 | Parshall............................ | 260/429 R |
| 3,458,547 | 7/1969 | Coffey............................... | 260/429 R |
| 3,515,757 | 6/1970 | Sibert................................ | 252/431 P |
| 3,547,984 | 12/1970 | Young............................... | 252/431 P |

OTHER PUBLICATIONS

Grimes, Carboranes, Academic Press, N.Y. pp. 207–249 (1970).
Kosolapoff et al., Organic Phosphorus Compounds, Wiley–Interscience, N.Y. vol. 1, pp. 488–489 (1972).
Booth, Advances in Inorganic Chem. and Radiochem. vol. 6, pp. 23 to 26, 1964.
J.A.C.S. V 88, pp. 2272–2282 (1966).
J.A.C.S. V 94, pp. 6679–6682 (1972).
Science, V 178, p. 462 (1972).

*Primary Examiner*—Helen M. S. Sneed
*Attorney, Agent, or Firm*—R. S. Sciascia; Paul N. Critchlow

[57] ABSTRACT

A family of stable hydrido-rhodium and iridium carboranes are described which are effective catalysts for the homogeneous hydrogenation, isomerization and hydroformylation of olefins and the hydrosilylation of ketones.

7 Claims, 5 Drawing Figures

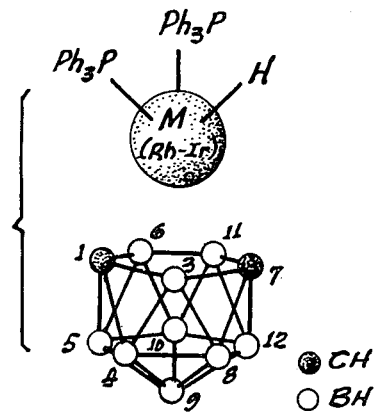

FIG. 1.

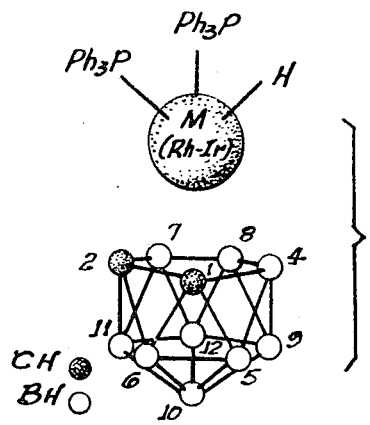

FIG. 2.

TABLE III

CATALYTIC HYDROSILYLATION REACTIONS $$RC(O)R' + Ph_2SiH_2 \rightarrow RCHR'(OSiHPh_2)$$

| CATALYST | SOLVENT | SUBSTRATE | REMARKS |
|---|---|---|---|
| NONE | THF | PhC(O)CH$_3$ | NO SILANE PRESENT, 1 atm OF H$_2$, NO CATALYST, NO REDUCTION |
| NONE | THF | PhC(O)CH$_3$ | NO REDUCTION |
| 1 | BENZENE | PhC(O)CH$_3$ | 55% REDUCTION |
| 1 | THF | PhC(O)CH$_3$ | 78% REDUCTION |
| 2 | THF | PhC(O)CH$_3$ | 100% REDUCTION |
| 2 | THF | PhCH$_2$C(O)CH$_3$ | 100% REDUCTION |
| 2 | THF | Me$_2$C=CHC(O)CH$_3$ | 100% REDUCTION, BOTH 1,2 AND 1,4 ADDITION. |
| 3 | THF | PhC(O)CH$_3$ | 100% REDUCTION |
| 5 | THF | PhC(O)CH$_3$ | 100% REDUCTION |

CONDITIONS: 55°, 1 atm OF N$_2$, 17 HR, 1.0 M IN Ph$_2$SiH$_2$, 0.6 M IN SUBSTRATE, 0.002 M IN CATALYST.

FIG. 5.

United States Patent [19]
Hawthorne et al.

[11] 3,976,596
[45] Aug. 24, 1976

[54] HYDRIDOMETALLIC CARBORANE CATALYTIC COMPOUNDS

[75] Inventors: Marion F. Hawthorne, Brentwood, Calif.; Timm E. Paxson, Houston, Tex.

[73] Assignee: The United States of America as represented by the Secretary of the Navy, Washington, D.C.

[22] Filed: Mar. 26, 1975

[21] Appl. No.: 562,070

[52] U.S. Cl. ................. 252/431 P; 260/429 R; 260/448.2 B; 260/497 R; 260/526 R; 260/561 R; 260/604 HF
[51] Int. Cl.$^2$ ................. B01J 31/12; C07F 15/00
[58] Field of Search .............. 260/429 R; 252/431 P

[56] References Cited
UNITED STATES PATENTS

| | | | |
|---|---|---|---|
| 3,418,346 | 12/1968 | Parshall | 260/429 R |
| 3,458,547 | 7/1969 | Coffey | 260/429 R |
| 3,515,757 | 6/1970 | Sibert | 252/431 P |
| 3,547,984 | 12/1970 | Young | 252/431 P |

OTHER PUBLICATIONS

Grimes, Carboranes, Academic Press, N.Y. pp. 207–249 (1970).
Kosolapoff et al., Organic Phosphorus Compounds, Wiley–Interscience, N.Y. vol. 1, pp. 488–489 (1972).
Booth, Advances in Inorganic Chem. and Radiochem. vol. 6, pp. 23 to 26, 1964.
J.A.C.S. V 88, pp. 2272–2282 (1966).
J.A.C.S. V 94, pp. 6679–6682 (1972).
Science, V 178, p. 462 (1972).

*Primary Examiner*—Helen M. S. Sneed
*Attorney, Agent, or Firm*—R. S. Sciascia; Paul N. Critchlow

[57] ABSTRACT

A family of stable hydrido-rhodium and iridium carboranes are described which are effective catalysts for the homogeneous hydrogenation, isomerization and hydroformylation of olefins and the hydrosilylation of ketones.

7 Claims, 5 Drawing Figures

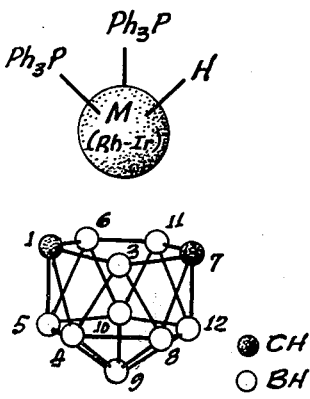
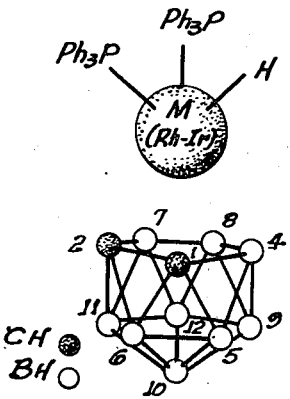

HYDRIDOMETALLIC CARBORANE CATALYTIC COMPOUNDS

BACKGROUND OF THE INVENTION

The present invention relates to metallocarboranes and, in particular to catalytic systems utilizing the metallocarboranes.

In recent years the discovery and utility of homogeneous hydrogenation, isomerization, hydrosilylation and hydrogen-deuterium exchange catalysts have expanded in scope to become one of the largest areas of endeavor in inorganic chemistry. To date, however, there apparently have been no reports of catalytic systems utilizing the very stable family of metallocarboranes and, consequently, there has been no known recognition of what appears to be a high potential value of the metallocarboranes catalysts in the petrochemical industry as well as their general applicability to many homogeneous catalytic transformations.

For reference purposes, the following publications discuss hydrogenation, isomerization, hydrosilylation and hydrogen-deuterium exchange catalysts:

J. Kwiatek in "Transition Metals in Homogeneous Catalysis", G. N. Schrauzer, Ed., Marcel Dekker, New York, N. Y., 1971, pp 13–51. B. R. James, "Homogeneous Hydrogenation," Wiley, New York, N.Y., 1973.

R. Cramer, J. Amer. Chem. Soc., 88, 2272 (1966), and references therein; R. Cramer, Ann. N. Y. Acad. Sci., 172, 507 (1971); B. Hudson, P. C. Taylor, D. E. Webster, and P. B. Well, J. Chem. Soc. A, 37 (1968).

A. J. Chalk, Ann. N. Y. Acad. Sci., 172, 533 (1971).
A. F. Thomas, "Deuterium Labeling in Organic Chemistry," Appleton-Century-Crofts, New York, N. Y., 1971, Chapter 6.

Also, the following references generally discuss metallocarboranes and their stability:

R. N. Grimes, "Carboranes," Academic Press, New York, N. Y., 1970 pp 207–232; M. F. Hawthorne and G. B. Dunks, Science, 178,462 (1972).

The present invention reports the discovery of a family of stable hydridometallic carborane catalysts for use particularly as homogeneous catalysts. The family includes compounds having the empirical formula $(PPh_3)_2HMC_2B_9H_{11}$ in which M is a metal. Also included are the substituted complexes having the formula $R(PPh_3)_2HMC_2B_9H_{10}$ in which R is a general designation for substances including $CH_3-$, $Ph-$, $CH_3CH_2OCH_2-$ and other alkyl and aryl moieties attached to carbon. In particular, the basic unsubstituted compound or complex includes two isomers in both of which the metal molecule represented by M of the empirical may be rhodium or iridium. Also, cobalt and ruthenium complexes having the same stereo chemistry as the rhodium and iridium complexes should demonstrate the same stability and effectiveness.

Analysis of the two isomers shows following formulations in which as already stated, the metal molecule M represents either rhodium or iridium;

I. $2,2-(PPh_3)_2-2-H-2,1,7-MC_2B_9H_{11}$ and
II. $3,3-(PPh_3)_2-3-H-3,1,2-MC_2B_9H_{11}$.

It is to be noted that these two complexes are numbered I and II and subsequent description will refer to them by these numbers. As will be apparent the rhodium isomers include complexes I and II and the same applies to the iridium isomers. The proposed stereo chemistry for the two isomers is shown in FIGS. 1 and 2 each of which depicts a carborane ligand coordinated to a metal which may be rhodium or iridium. In the ligand, the BH molecules are shown by a clear circle while the CH molecules are a darkened circle. FIG. 1 represents complex I which is a 1,7 isomer, while FIG. 2 represents the II which is a 1,2 isomer.

Complexes I and II can be prepared in high yields from the $7,9,-C_2B_9H_{12}^-$ and $7,8-C_2B_9H_{12}^-$ monoanions respectively, utilizing the scheme diametrically depicted below:

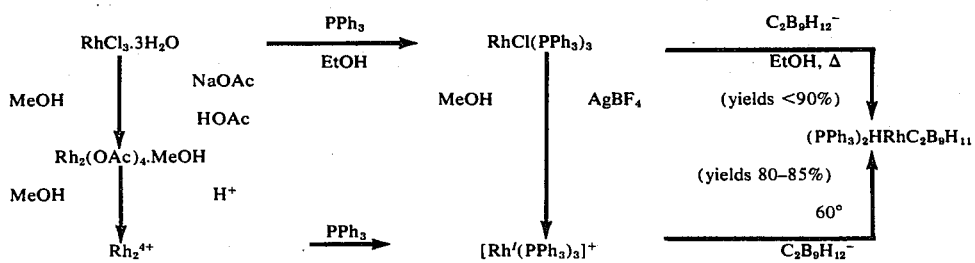

As shown in the above diagram, when a methanol solution of the tris(triphenylphosphine)rhodium(I) cation is allowed to react at 60° with a methanolic solution of either $(CH_3)_3NH^+[7,9-C_2B_9H_{12}]^-$ (Ia) or $(CH_3)_3NH^+_-[7,8-C_2B_9H_{12}]$ — (IIa) high yields (>80%) of yellow crystalline products I and II, respectively, were obtained. Compounds I and II could also be obtained by treatment of $[(C_6H_5)_3P]_3RhCl$ with a methanolic solution of $AgBF_4$ and subsequent reaction with Ia or IIa (yields > 85%) or by direct reaction of Ia or IIa with $[(C_6H_5)_3P]_3RhCl$ in alcoholic solutions (yields > 90%).

The iridacarboranes, compounds I and II, are prepared using the synthetic routes outlined below:

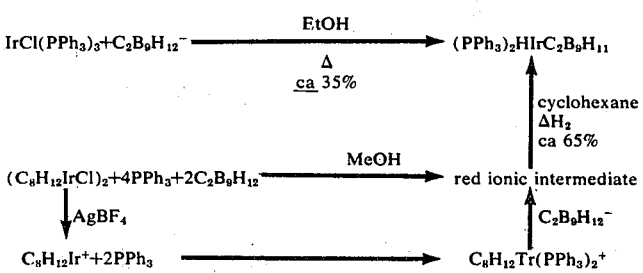

Deuterium exchange. As reported in a Journal of the American Chemical Society, 96, 4676 (1974), Elvin L. Hoel, M. Frederick Hawthorne, Compounds 1 and 2 effect deuteration of $1,2-C_2B_{10}H_{12}$ at least one order of magnitude faster than any other presently known catalyst. The following Table provides a comparison of selected catalysts with $1,2-C_2B_{10}H_{12}$ as a substrate:

Table I

Comparison of Selected Catalysts with $1,2-C_2B_{10}H_{12}$ as Substrate

| System | Catalyst | Conditions[a] | Av no. of D in product[b] |
|---|---|---|---|
| 1 | 10% Pd on C (1 g) | 3 days, 100° | 2 |
| 2 | $(PPh_3)_3RhCl$[c] | 18 hr, 80° | 2 |
| 3 | $(PPh_3)_3RuHCl$ | 18 hr, 80° | 5 |
| 4 | $(PPh_3)_3RuHCl$ | 3 days, 100° | 8 |
| 5 | I | 1 day, 65° | 10 |
| 6 | II | 1 day, 65° | 10 |

[a]Except where noted, reactions were with 1 mmol of $1,2-C_2B_{10}H_{12}$ and 0.05 mmol of catalyst in 20 ml of toluene with $D_2$ bubbling at ~3 ml/min.
[b]Estimated from ir, $^{11}B$ nmr, and mass spectra.
[c]Formed nearly insoluble dimer and slowly decomposed under these conditions.

The results obtained with the catalytic systems described in the above Table I provide an example of the relative activity and selectivity exhibited by these catalysts with a variety of substrates. The tests using present Compounds I and II are included. The order of rates of deuterium incorporation at the four chemically nonequivalent sets of sites in $1,2-C_2B_{10}H_{12}$ was followed by 80.5-MHz $^{11}B$ nmr spectroscopy. With increasing deuterium exchange at a site represented by a given resonance, the doublet due to hydrogen coupling collapsed smoothly to a singlet.

The investigations which have been described appear to effectively establish the potential value of metallocarboranes catalysts for effecting isomerization, hydrogenation, hydrosilylation and hydroformulation of various substrates. The carborane cage evidently stabilizes the complexes and allows these species to function in catalytic reactions. With their intrinsic stabilities in the solid state and in solution, coupled with their facile recovery, this class of catalysts should provide very high conversion numbers and reusability. Obviously, they are of high potential value in the petrochemical industry. Also, the preliminary data of the reactions catalyzed by the compounds certainly suggests that they may find general applicability to homogeneous catalytic transformations.

Obviously many modifications and variations of the present invention are possible in the light of the above teachings. It is therefore to be understood that within the scope of the appended claims the invention may be practiced otherwise than as specifically described.

We claim:

1. A hydridometallic compound for use as a catalyst, said compound being selected from a group consisting of isomers of $R(PPh_3)_2HMC_2B_9H_{10}$ wherein M is a metal selected from a group consisting of rhodium and iridium and wherein R is selected from a group consisting of $CH_3—$, Ph, $CH_3$ and $CH_2OCH_2—$.

2. An hydridometallic carborane compound for use as a catalyst, said compound being selected from a group consisting of isomers of $(PPh_3)_2HMC_2B_9H_{11}$ wherein M is a metal selected from a group consisting of rhodium and iridium.

3. The compound of claim 2 wherein said isomers consist of $2,2-(PPh_3)_2-2-H-2,1,7-MC_2B_9H_{11}$ and $3,3(PPh_3)_2-3-H-3,1,2-MC_2B_9H_{11}$.

4. An homogeneous catalytic solution for the hydrogenation, isomerization and hydroformylation of olefins and the hydrosilylation of ketones comprising:
   an hydridometallic carborane compound selected from a group consisting of isomers of $(PPh_3)_2HMC_2B_9H_{11}$ wherein M is a metal selected from a group consisting of rhodium and iridium, and
   a solvent for said compound.

5. The solution of claim 4 wherein said isomers consist of $2,2-(PPh_3)_2-2-H-2,1,7-MC_2B_9H_{11}$ and $3,3(PPh_3)_2-3-H-3,1,2-MC_2B_9H_{11}$.

6. The solution of claim 5 wherein said solvent is tetrahydrofurane.

7. The solution of claim 5 wherein said solvent is benzene.

* * * * *